United States Patent [19]

Mallion

[11] 3,935,240

[45] Jan. 27, 1976

[54] CYCLOPENTYLHEPTENOIC ACIDS AND DERIVATIVES

[75] Inventor: Keith Blakeney Mallion, Macclesfield, England

[73] Assignee: Imperial Chemical Industries Limited, London, England

[22] Filed: Oct. 26, 1973

[21] Appl. No.: 410,090

[30] Foreign Application Priority Data

Nov. 10, 1972 United Kingdom............... 52010/72
Jan. 15, 1973 United Kingdom................. 2033/73
Aug. 15, 1973 United Kingdom............... 39578/73

[52] U.S. Cl..... 260/469; 260/240 R; 260/326.13 R; 260/340.7; 260/340.9; 260/343.2 R; 260/343.3; 260/345.8; 260/346.2 R; 260/347.2; 260/347.3; 260/347.4; 260/347.7; 260/347.8; 260/410; 260/468 D; 260/471 R; 260/476 R; 260/488 R; 260/514 D; 260/558 S; 260/559 R; 260/570.9; 260/571; 260/574; 260/576; 260/577; 260/598; 260/609 R; 260/609 B; 260/612 D; 260/617 R; 260/611 R; 260/618 R; 260/618 D; 260/611 A; 260/612 R

[51] Int. Cl.².......................................... C07C 69/76
[58] Field of Search............ 260/469, 468 D, 476 R, 260/514 D, 471 R

[56] References Cited
UNITED STATES PATENTS
3,887,587   6/1975   Schaaf et al. ................... 260/468 D

*Primary Examiner*—James A. Patten
*Assistant Examiner*—Jane S. Myers
*Attorney, Agent, or Firm*—Cushman, Darby & Cushman

[57] ABSTRACT

The disclosure relates to novel intermediates, for use in the manufacture of known prostaglandins and prostaglandin-like compounds, for example aldehydes such as methyl 7-[2β-formyl-3α-hydroxy-5α-(4-phenylbenzoyloxy)cyclopent-1α-yl]hetp-5-cis-enoate and enones such as methyl 15-oxo-9α,11α-di(4-phenylbenzoyloxy)-5-cis,13-trans-prostadienoate, processes for their manufacture, and their conversion to prostaglandins or prostaglandin-like compounds.

6 Claims, No Drawings

CYCLOPENTYLHEPTENOIC ACIDS AND DERIVATIVES

This invention relates to chemical intermediates, and in particular it relates to chemical intermediates which are useful in the manufacture of prostaglandins and prostaglandin-like compounds.

According to the invention, there is provided as a chemical intermediate an aldehyde of the formula:

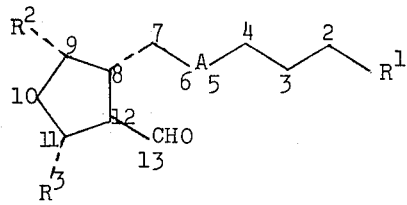

I wherein $R^1$ is a carboxy or hydroxymethyl radical, or an alkoxycarbonyl radical of up to 11 carbon atoms, A is an ethylene or cis-vinylene radical, and $R^2$ and $R^3$, which may be the same or different, are hydroxy radicals or protected hydroxy radicals, or $R^1$ and $R^2$ together form an oxycarbonyl radical, in which an oxygen atom is bonded to carbon atom 9, and the carbon atom is bonded to carbon atom 2, and bearing 0 or 1 alkyl substituent of 1 to 4 carbon atoms on carbon atom 2, 3 or 4, provided that when $R^1$ is a methoxycarbonyl radical, and either $R^2$ is an acetoxy radical and $R^3$ is a tetrahydropyran-2-yloxy radical, or $R^2$ is a 4-phenylbenzoyloxy radical and $R^3$ is an acetoxy radical, A is a vinylene radical.

A suitable value for $R^1$ when it is an alkoxycarbonyl radical is, for example a methoxycarbonyl, n-butoxycarbonyl or n-decyloxycarbonyl radical. A suitable value for $R^2$ or $R^3$, when either is a protected hydroxy radical, is, for example, an alkanoyloxy radical of 1 to 10 carbon atoms, for example, an acetoxy radical; an aroyloxy radical of up to 15 carbon atoms, for example a benzoyloxy radical, optionally substituted, for example a 4-phenylbenzoyloxy or 3,5-dinitrobenzoyloxy radical; or a tetrahydropyran-2-yloxy radical.

A suitable alkyl substituent on carbon atom 2, 3 or 4 is, for example, the methyl radical.

It will be observed that the compounds of the formula I contain at least four asymmetric carbon atoms, namely carbon atoms 8, 9, 11 and 12, the configurations of which are specified in formula I, and that carbon atom 2, 3 or 4 may also be asymmetrically substituted, so that it is clear that such compounds can exist in at least two optically active forms. It is to be understood that this invention relates to the racemic form of the compounds of formula I and any optically active form which is a precursor of a useful, optically active, prostaglandin or prostaglandin-like compound, it being a matter of common general knowledge how the optically active forms may be obtained.

Preferred compounds of the invention of the formula I are methyl 7-[2β-formyl-3α,5α-di(4-phenylbenzoyloxy)cyclopent-1α-yl]hept-5-cis-enoate, methyl 7-[2β-formyl-3α,5α-dihydroxycyclopent-1α-yl]hept-5-cis-enoate, methyl 7-[2β-formyl-3α-hydroxy-5α-(4-phenylbenzoyloxy)cyclopent-1α-yl]heptanoate, methyl 7-[2β-formyl-3α-hydroxy-5α-(4-phenylbenzoyloxy)cyclopent-1α-yl]hept-5-cis-enoate and 7-[3α-(3,5-dinitrobenzoyloxy)-2β-formyl-5α-hydroxycyclopent-1α-yl]hept-5-cis-enoic acid lactone.

According to a further feature of the invention there is provided a process for the manufacture of the chemical intermediate of the formula I which comprises the acid hydrolysis of an acetal of the formula:

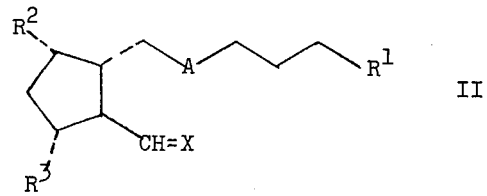

II wherein A, $R^1$, $R^2$ and $R^3$ have the meanings stated above, and X represents two alkoxy radicals, each of up to 5 carbon atoms, for example methoxy radicals, an alkylenedioxy radical of 2 to 6 carbon atoms, for example an ethylenedioxy, trimethylene-1,3-dioxy or 2,2-dimethyltrimethylene-1,3-dioxy radical.

The hydrolysis is conveniently carried out in a two-phase system comprising concentrated hydrochloric acid as the aqueous phase, and 2% by volume of isopropanol in chloroform as the immiscible organic phase. The starting materials of the formula II may be prepared from known compounds by several different routes using standard procedures of organic chemistry. By way of example only, three alternative preparations of starting materials II will be described.

4β-Dimethoxymethyl-2,3,3aβ,6aβ-tetrahydro-5α-hydroxy-6β-iodo-2-oxocyclopenteno[b]furan (III) is treated with tributyl tin hydride to give the de-iodinated lactone IV. The 5α-hydroxy group is protected as the tetrahydropyran-2-yl ether V, the lactone is reduced to the lactol VI, using di-isobutyl aluminium hydride, and the lactol is reacted with (4-carboxybutyl)triphenylphosphonium bromide to give the cyclopentanol derivative VII, which on methanolysis forms a methyl ester with concomitant hydrolysis of the tetrahydropyranyl ether group to give a starting material of the formula II ($R^1$ = methoxycarbonyl, $R^2$ = $R^3$ = hydroxy, A = cis-vinylene).

Additionally, the two hydroxy groups of the above-described starting material II may be esterified to give a starting material of the formula II ($R^1$ = methoxycarbonyl, $R^2$ = $R^3$ = alkanoyloxy or aroyloxy), or the methoxycarbonyl group may be reduced, for example with lithium aluminium hydride, to give a starting material of the formula II ($R^1$ = hydroxymethyl, $R^2$ = $R^3$ = hydroxy, A = cis-vinylene).

An alternative process for the manufacture of starting materials II wherein A is cis-vinylene from the cyclopentenofuran III involves deiodination to IV as described above, and reduction of the deiodinated lactone to the hydroxy-lactol VIII. Reaction of this hydroxy-lactol with (4-carboxybutyl)triphenylphosphonium bromide give a cyclopentanediol derivative IX, that is, a starting material II wherein A is cis-vinylene, $R^2$ and $R^3$ are hydroxy, and X represents two methoxy radicals.

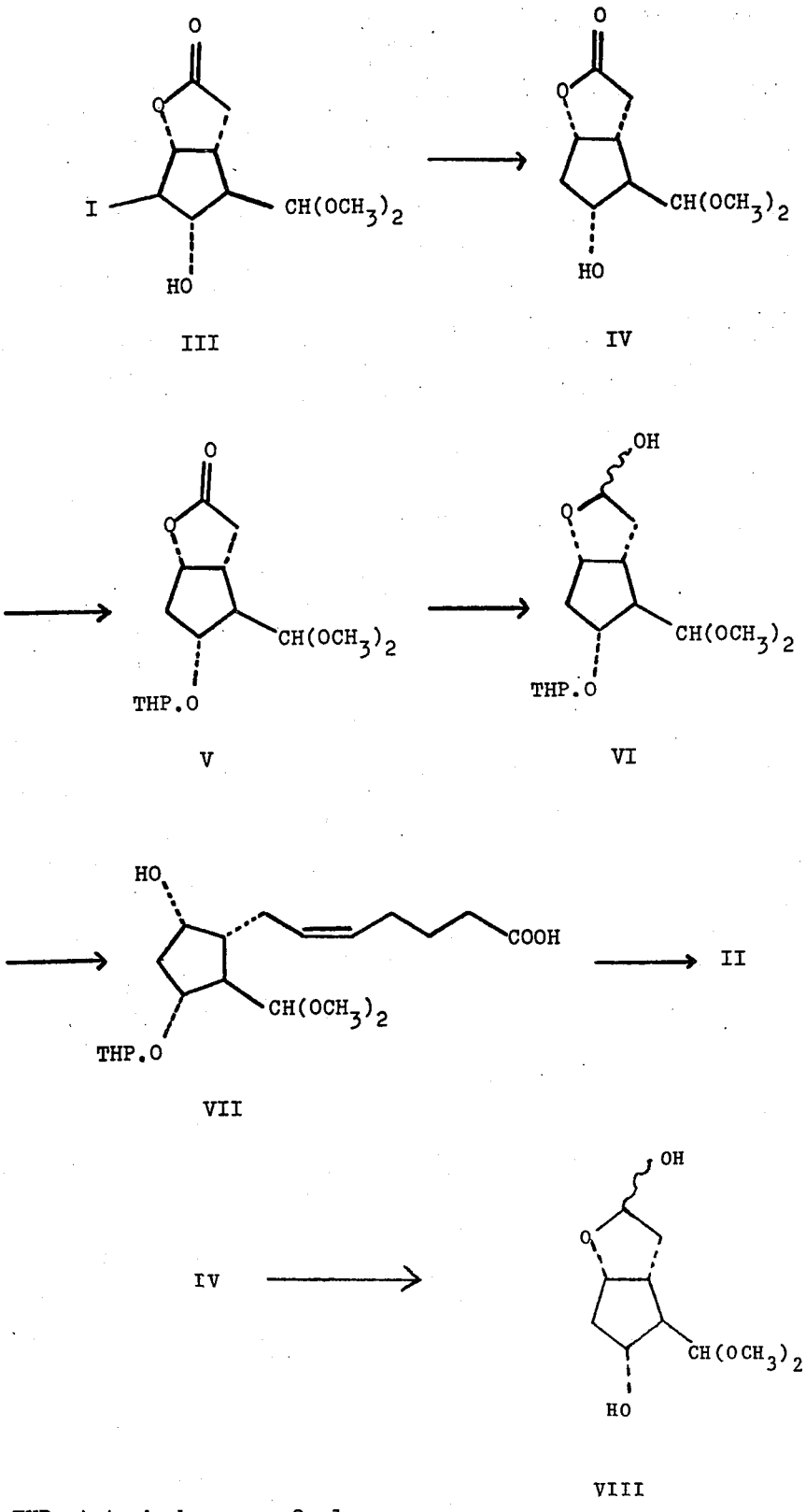

THP= tetrahydropyran-2-yl.

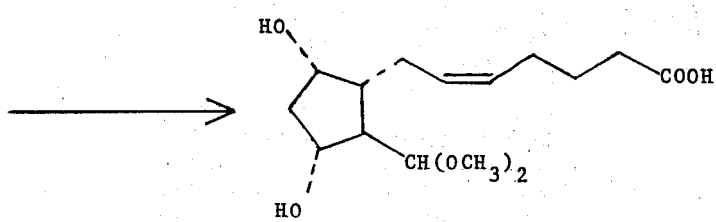

IX

Additionally, methanolysis of the cyclopentanediol derivative IX gives a methyl ester, (II, A = cis-vinylene, $R^2 = R^3 =$ hydroxy, X = two methoxy radicals and $R^1 =$ methoxycarbonyl), and reduction of the methyl ester, for example with lithium aluminium hydride, gives a starting material II (A = cis-vinylene, $R^2 = R^3 =$ hydroxy, X represents two methoxy radicals and $R^1 =$ hydroxymethyl).

Starting materials of the formula II wherein A is the ethylene radical may be prepared from the cyclopentanol derivative VII by esterification to the methyl ester X with diazomethane, conversion to the 5α-(4-phenylbenzoyloxy) compound XI and hydrolysis of the tetrahydropyranyl radical to the hydroxy compound XII which is hydrogenated to required starting material II ($R^1 =$ methoxycarbonyl, $R^2 =$ 4-phenylbenzoyloxy, $R^3 =$ hydroxy and A = ethylene).

VII ⟶ 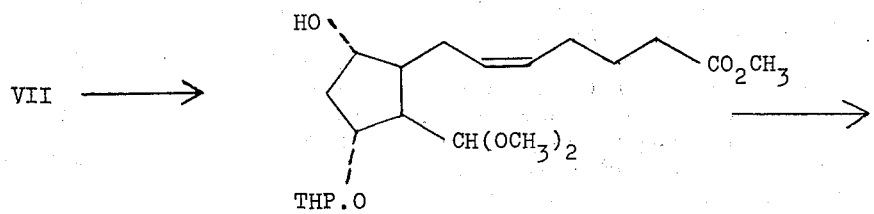

X

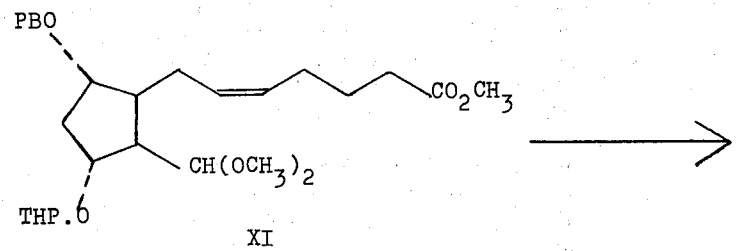

XI

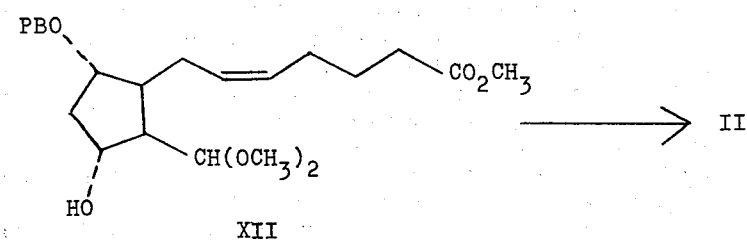 ⟶ II

XII

PB = 4-phenylbenzoyl

According to a further feature of the invention there is provided a process for the manufacture of a prostaglandin or prostaglandin-like compound of the formula:

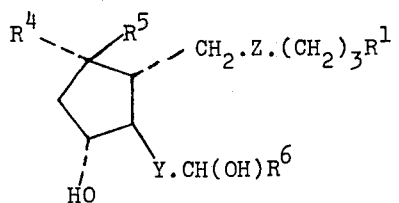

XIII wherein $R^1$ has the meaning stated above, $R^4$ is a hydroxy radical or an alkanoyloxy radical of 1 to 4 carbon atoms and $R^5$ is a hydrogen atom, y is an ethylene or trans-vinylene radical, Z is an ethylene or cis-vinylene radical, and $R^6$ is: a branched or unbranched alkyl radical of 4 to 10 carbon atoms; a radical of the formula $-A^1.OR^7$, wherein $A^1$ is an alkylene radical of 1 to 9 carbon atoms and $R^7$ is an alkyl radical of 1 to 9 carbon atoms or a cycloalkyl radical of 5 to 7 carbon atoms, provided that $A^1$ and $R^7$ together contain not more than 10 carbon atoms;

a radical of the formula $-A^2R^8$, wherein $A^2$ is a direct bond or an alkylene radical of 1 to 3 carbon atoms, and $R^8$ is an aryl radical which is unsubstituted or which is substituted by halogen atoms, nitro radicals, alkyl, halogenoalkyl, alkoxy or alkoxyalkyl radicals each of 1 to 3 carbon atoms or dialkylamino radicals wherein each alkyl is of 1 to 3 carbon atoms;

a radical of the formula $-A^3.A^4.R^9$, wherein $A^3$ is an alkylene radical of 1 to 3 carbon atoms bearing as substituents 0, 1 or 2 alkyl radicals each of 1 to 3 carbon atoms, $A^4$ is an oxygen or sulphur atom, a sulphinyl radical or an alkylimino radical of up to 4 carbon atoms, and $R^9$ is an aryl, benzyl or furfuryl radical optionally substituted by hydroxy, nitro or phenyl radicals, halogen atoms, alkyl, alkenyl, halogenoalkyl, alkoxy, alkenyloxy, or acylamino radicals of 1 to 4 carbon atoms or dialkylamino wherein each alkyl is of 1 to 3 carbon atoms; or a radical of the formula $-A^3.A^5.R^{10}$, wherein $A^3$ has the meaning stated above, $A^5$ is an oxygen or sulphur atom, a sulphinyl, sulphonyl, imino or alkylimino radical of up to 4 carbon atoms or a direct bond, or $A^3$ and $A^5$ are each a direct bond, and $R^{10}$ is an aromatic heterocyclic radical of one or two 5- or 6-membered rings, containing in one ring only, 1 or 2 non-adjacent nitrogen hetero-atoms, and optionally bearing 1 to 3 alkyl radicals or halogen atoms as substituents; which compound contains 0 or 1 alkyl radical of 1 to 4 carbon atoms as substituents in the trimethylene group; and for those compounds wherein $R^1$ is a carboxy radical, the pharmaceutically acceptable salts thereof;

which comprises reacting a compound of the formula I with a phosphonate of the formula $(R^{11}O)_2PO.CH_2COR^6$ in the presence of a strong base, or with a phosphorane of the formula $Ph_3P{:}CH.COR^6$, wherein $R^6$ has the meaning stated above and $R^{11}$ is an alkyl radical of 1 to 4 carbon atoms, to give an enone which is reduced, for example with zinc borohydride, aluminium tri-isopropoxide or di-isobornyloxy aluminium isopropoxide, to a prostaglandin or prostaglandin-like compound of the formula XIII.

According to a further feature of the invention, there is provided the use of a compound of the invention of the formula I as an intermediate for the manufacture of a prostaglandin or a prostaglandin-like compound of the formula XIII wherein $R^4$ and $R^5$ together form the oxo radical, and $R^1$, Z, Y and $R^6$ have the meanings stated above, which comprises reacting an aldehyde of the formula I wherein $R^2$ is a protected hydroxy radical, for example the 4-phenylbenzoyloxy radical, and $R^3$ is a hydroxy radical, with a phosphonate or a phosphorane as described above to give an enone which is reduced to a prostaglandin-like compound of the formula XIII wherein $R^4$ is a protected hydroxy radical and $R^5$ is a hydrogen atom. This compound XIII is reacted with 2,3-dihydropyran to give the corresponding bis(tetrahydropyranyl ether), the 4-phenylbenzoyloxy radical is hydrolysed to a hydroxy radical, the hydroxy compound is oxidised, for example with Jones' reagent or Collins' reagent, to the corresponding 9-oxo compound, and hydrolysis of the tetrahydropyranyl ethers gives a prostaglandin-like compound of the formula XIII wherein $R^4$ and $R^5$ together form the oxo radical.

The above-mentioned enone is itself a novel compound and a valuable intermediate. Thus, according to a further feature of the invention there is provided an enone of the formula:

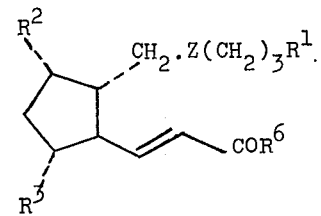

XIV wherein $R^1$, $R^2$, $R^3$, $R^6$ and Z have the meanings stated above, which contains 0 or 1 alkyl radical of 1 to 4 carbon atoms as substituent in the trimethylene group.

Suitable values for $R^1$, $R^2$ and $R^3$ are those stated above.

Particular enones of the invention are methyl 15-oxo-9α,11α-di(4-phenylbenzoyloxy)-5-cis,13-trans-prostadienoate, methyl 15-oxo-9α,11α-di(4-phenylbenzoyloxy)-16-(3-trifluoromethylphenoxy)-17,18,19,20-tetranor-5-cis,13-trans-prostadienoate, methyl 9α,11α-dihydroxy-15-oxo-5-cis,13-trans-prostadienoate, methyl 15-(4-methoxymethylphenyl)-15-oxo-9α,11α-di(4-phenylbenzoyloxy)-16,17,18,19,20-pentanor-5-cis,13-trans-prostadienoate, methyl 11α-hydroxy-16-(indol-5-yloxy)-15-oxo-9α-(4-phenylbenzoyloxy)-17,18,19,20-tetranor-13-trans-prostenoate, 11α-(3,5-dinitrobenzoyloxy)-9α-hydroxy-15-oxo-16-(3-trifluoromethylphenoxy)-17,18,19,20-tetranor-5-cis,13-trans-prostadienoic acid 1,9α-lactone and methyl 11α-hydroxy-15-oxo-9α-(4-phenylbenzoyloxy)-5-cis,13-trans-prostadienoate.

It is to be understood that the compounds XIV can exist in optically active forms in the same way as the compounds I, and that this invention relates to both the racemate and the optically active form, particularly the laevorotatory isomer, which is the precursor of prostaglandins of the naturally occurring series.

According to a further feature of the invention there is provided a process for the manufacture of an enone of the formula XIV which comprises the reaction of an aldehyde of the formula I, wherein A, $R^1$, $R^2$ and $R^3$ have the meanings stated above, with a phosphonate of the formula $(R^{11}O)_2PO.CH_2COR^6$ or a phosphorane of the formula $Ph_3P:CH.COR^6$, wherein $R^6$ and $R^{11}$ have the meanings stated above, in the presence of a strong base.

The use of a compound of the formula I in the synthesis of prostaglandins and prostaglandin-like compounds offers advantages over the normal synthesis in that the sidechain containing $R^6$ is added as the final stage. The present invention is thus particularly convenient for the preparation of prostaglandin-like compounds wherein $R^6$ is sensitive to acid, to di-isobutylaluminium hydride or to Wittig reagents, which in the normal synthesis are reagents which are used after the group $R^6$ has been introduced into the molecule. The present invention is also particularly convenient for the manufacture of prostaglandins and prostaglandin-like compounds of the 1-series, that is, compounds of the formula XIII wherein Z is the ethylene radical, in that the double bond in the carboxyl side chain can be reduced directly, whereas in the normal synthesis a selective reduction is necessary to reduce the 5-cis, but not the 13-trans, double bond.

The invention is illustrated but not limited by the following Examples. Throughout the Examples, $R_F$ values refer to silica gel plates supplied commercially by Merck of Darmstadt, and the spots were detected either by fluorescence under ultra-violet radiation, or by spraying the plates with a solution of ceric ammonium nitrate in sulphuric acid.

EXAMPLE 1

Methyl 7-[2β-dimethoxymethyl-3α,5α-di-(4-phenylbenzoyloxy)-cyclopent-1α-yl]hept-5-cis-enoate (500mg.) was vigorously stirred under argon for 10 minutes in a two-phase system consisting of 2% isopropanol in chloroform (20ml.) and concentrated hydrochloric acid (10ml.). The chloroform layer was separated and the aqueous layer was extracted with chloroform (20ml.). The organic layers were combined, washed successively with aqueous saturated sodium bicarbonate (20ml.) and saturated brine (10ml.), dried over magnesium sulphate and filtered, and the solvent was evaporated. The oily residue crystallised on drying under high vacuum to give methyl 7-[2β-formyl-3α,5α-di-(4-phenylbenzoyloxy)cyclopent-1α-yl]hept-5-cis-enoate, $R_F$ on Merck silica gel $G_F$ 254 plates was 0.4 (5% ethyl acetate in toluene). The n.m.r. spectrum in deuteriochloroform was consistent with the required structure, and showed the following principal signals (δ values):

| 3.51, | 3H, | singlet, | methyl ester. |
|---|---|---|---|
| 5.3–5.6, | 4H, | multiplet, | >CH—O— and olefinic protons. |
| 7.8–8.0, | 2H, | } doublets, |  |
| 8.0–8.2, | 2H, | | |
| 7.22–7.73, | 14H, | multiplet, | rest of aromatic protons |
| 10.01–10.14, | 1H, | doublet, | —CHO |

An analytical sample, m.p. 93–97°C., was obtained by triturating the above-described product with ether.

The methyl 7-[2β-dimethoxymethyl-3α,5α-di-(4-phenylbenzoyloxy)cyclopent-1α-yl]hept-5-cis-enoate used as starting material in the above process may be prepared as follows:

4β-Dimethoxymethyl-2,3,3aβ,6aβ-tetrahydro-5α-hydroxy-6β-iodo-2-oxocyclopenteno[b]furan (III, 4.0g.) in dry toluene (40ml.) was stirred under argon at 80°C. with tri-n-butyl tin hydride (6.6g.) for 18 hours. The solvent was evaporated under reduced pressure and the residue was stirred with petroleum ether (b.p. 40°–60°C., 100ml.) for 30 minutes. The solvent was decanted and the residual oil was chromatographed on "Florisil" (trade mark) silica (50g.). Elution with mixtures containing 25% ethyl acetate in toluene and finally with ethyl acetate gave 4β-dimethoxymethyl-2,3,3aβ,6aβ-tetrahydro-5α-hydroxy-2-oxocyclopenteno[b]furan as an oil, $R_F$ = 0.3 (20% acetone in chloroform). The n.m.r. spectrum in deuteriochloroform showed the following characteristic peaks (δ values):

| 3.40 and 3.42, | 6H, 2 singlets, methoxy |
| 4.04–4.36 | { 1H, multiplet, 5β proton |
| | 1H, doublet, —CH(OMe)₂ |
| | 1H, multiplet, 6aβ proton |

4β-Dimethoxymethyl-2,3,3aβ,6aβ-tetrahydro-5α-hydroxy-2-oxocyclopenteno[b]furan (IV,4.01g.) was stirred under argon in dry toluene (30ml.), and the resulting solution was treated with an excess of freshly distilled dihydropyran (17ml.), followed by 2.0ml. of a 0.1% w/v solution of toluene-p-sulphonic acid in dry tetrahydrofuran. After ¾ hour, the mixture was treated with pyridine (0.50ml.) and then partitioned between ethyl acetate (150ml.) and saturated sodium bicarbonate (75ml.). The organic layer was separated, washed with saturated brine (50ml.), dried over magnesium sulphate and filtered, and the solvent was evaporated to give a crude lactone, 4β-dimethoxy-methyl-2,3,3aβ,-6aβ-tetrahydro-2-oxo-5α-tetrahydropyran-2-yloxy)-cyclopenteno[b]furan, (V),$R_F$ = 0.70 (20% acetone in chloroform). The crude lactone (V, 6.2g.) was dissolved by stirring in dry dimethoxyethane (120ml.) under argon at about −60°C. (chloroform — 'Drikold' (trade mark) cooling bath), and 1.7M di-isobutylaluminium hydride (11.2 ml.) was added. After 30 minutes, methanol (3ml.) was added, the mixture was allowed to warm up to room temperature, and was partitioned between ethyl acetate (600ml.) and 1:1 saturated brine/water (300ml.). The whole mixture was filtered through "Hyflo" (trade mark) kieselguhr and the two phases were separated. The aqueous phase was reextracted with ethyl acetate (300ml.) and the combined organic layers were washed with water (100ml.), dried over magnesium sulphate and filtered, and the solvents were evaporated to give the crude lactol (VI) 4β-dimethoxymethyl-2,3,3aβ,6aβ-tetrahydro-2-hydroxy-5α-(tetrahydropyran-2-yloxy)-cyclopenteno[b]furan, as an oil, $R_F$ = 0.4 (20% acetone in chloroform).

A stirred solution of (4-carboxybutyl)triphenylphosphonium bromide (24.8g.) in dry dimethylsulphoxide (DMSO, 30ml.) was treated slowly under argon and with cooling in an ice-water bath, with 2M methanesulphinylmethyl sodium in DMSO (54.5ml., 2.5 equivalents) to form a solution of the corresponding ylide. The crude lactol (VI, 6.3g.) in dry DMSO (150ml.) was then added to the ylide solution at room temperature. The mixture was stirred for 1¼ hours, then water (1ml.) was added. The DMSO was then evaporated at high vacuum at a temperature not exceeding 50°C. The residual gum was partitioned between ether (4 × 225ml.) and water (150ml.). The aqueous layer was separated, acidified with 2N oxalic acid to approximately pH 4, and then extracted with 1:1 mixture of ether and pentane (3 × 300ml.). The extracts were washed with saturated brine (150ml.) dried over magnesium sulphate and filtered, and the solvent was evaporated to give the crude acid (VII) 2β-dimethoxymethyl-5α-hydroxy-3α-(tetrahydropyran-2-yloxy)cyclopent-1α-ylhept-5-cis-enoic acid as an oil, suitable for use in the next stage of the synthesis. A sample was purified by chromatography on silica (70:1) eluting the product with 2% methanol in toluene as an oil, $R_F = 0.4$ (5% methanol in methylene chloride). The n.m.r. spectrum in deuteriochloroform showed the following characteristic peaks (δ values):

3.35, 6H, singlet, methoxy
3.3–3.65, 1H,
3.68–4.0, 1H,
4.00–4.19, 2H,   } multiplets, >CH—O—
4.19–4.38, 1H,
4.6–4.8, 1H,
5.09–5.78, 2H, multiplet, olefinic protons The crude acid (VII, 4.48g.) in methanol (45ml.) was stirred under argon at room temperature with toluene-p-sulphonic acid (240mg.) for 2¾ hours. The solution was then partitioned between ethyl acetate (300ml.) and saturated sodium bicarbonate (60ml.) followed by saturated brine (60ml.). The organic phase was dried over magnesium sulphate and filtered, and the solvent was evaporated to leave a crude ester-diol, methyl 7-[2β-dimethoxymethyl-3α,5α-dihydroxycyclopent-1α-yl]-hept-5-cis-enoate as an oil, $R_F = 0.65$ (10% methanol in methylene chloride). The n.m.r. spectrum in deuteriochloroform showed the following principal peaks (δ values):

3.39, 6H, singlet,
                            } 3 methyl groups
3.64, 3H, singlet,
4.03–4.3, 3H,   { multiplet,  >CH—O—
                  doublet,    >CH(OMe)₂
5.1–5.7, 2H, multiplet, olefinic protons The crude ester-diol (3.3g.) was dissolved in dry pyridine (50ml.) under argon, and treated with p-phenylbenzoyl chloride (9.2g.) and the mixture was stirred for 17 hours. Water (0.8ml.) was then introduced and stirring was continued for 3–4 hours. The mixture was evaporated under reduced pressure and toluene was added to assist azeotropic removal of the pyridine. The residue was partitioned between toluene (300ml.) and saturated sodium bicarbonate solution (150ml.). The whole mixture was filtered through "Hyflo" and the organic phase was separated. The aqueous layer was extracted with toluene (150ml.), and the organic extracts were combined washed with brine (100ml.), dried over magnesium sulphate, and filtered, and the solvent was evaporated to leave a solid crystalline residue. This was thoroughly triturated with methanol (70ml.), the mixture was filtered, and the product was washed with more methanol (3 × 10ml.) to give the dimethyl acetal, methyl 7-[2β-dimethoxymethyl-3α,-5α-di-(4-phenylbenzoyloxy)cyclopent-1α-yl]hept-5-cis-enoate as a white solid, m.p. 104°–106.5°C., $R_F =$ 0.5 (5% acetone in toluene). The n.m.r. spectrum in deuteriochloroform showed the following characteristic signals (δ values):

3.41,       3H,   singlet  ⎫
3.47,       3H,   singlet  ⎬ methyls
3.52,       3H,   singlet  ⎭
4.59–4.61,  1H,   doublet, >CH(OMe)₂
5.17–5.70,  4H,   multiplet, 2 × >CH—O— and 2 olefinic protons 7.80–8.00,  2H,  ⎫
                 ⎬ doublet, 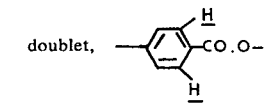
8.00–8.20,  2H,  ⎭

An analytical sample recrystallised three times from ethanol has m.p. 105°–107°C.

EXAMPLE 2

A solution of dimethyl 2-oxoheptylphosphonate (119mg. 1.5 equivalent) in dimethoxyethane (2.0ml.) was stirred under argon and cooled in a chloroform/'-Drikold' bath, and treated with 2.2M butyl-lithium in hexane (208µl.) followed after a few minutes by a solution of methyl 7-[2β-dimethoxymethyl-3α,5α-di(4-phenylbenzoyloxy)cyclopent-1α-yl]hept-5-cis-enoate (225.7mg.), also in dimethoxyethane (1.5ml.). The cooling bath was then removed, and after 2 hours a few drops of acetic acid and then water (200µl.) was added to adjust the pH to about 6. The solvent was evaporated under reduced pressure and the residue was partitioned between water (15ml.) and ethyl acetate (1 × 30ml., 1 × 15ml.). The organic layer was separated, washed with water (10ml.) then dried over magnesium sulphate, and filtered, and the solvent was evaporated to give a viscous oil. This oil was purified either by chromatography on "Florisil" (2g.) eluting with 5% ethyl acetate in toluene or by trituration with methanol (10ml.), to afford the enone, methyl 15-oxo-9α,11α-di(4-phenyl-benzoyloxy)-5-cis,13-trans-prostadienoate, as a white solid of analytical purity, m.p. 75–77.5°C., $R_F = 0.85$ (ether) or ~ 0.5 (5% ethyl acetate in toluene). The n.m.r. spectrum in deuteriochloroform showed the following principal peaks (δ values):

0.73–1.01,  3H,  triplet,        —CH₃
3.53,       3H,  singlet,        —COOCH₃
5.2–5.6,    4H,  multiplet,      cis olefinic protons and >CH—O—
6.12–6.29,  1H,  doublet,        =CH.CO—
6.70–7.03,  1H,  pair of doublets, —CH=CH.CO—

7.86–8.02,  2H,  doublet ⎫
                         ⎬ 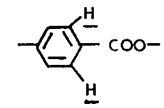
8.02–8.23,  2H,  doublet ⎭

7.20–7.73,  14H, multiplet,     rest of aromatic protons

The enone (50mg.) was stirred in dry toluene (1.0ml.) under argon at room temperature, and treated with a 0.323M solution of di-isobornyloxyaluminium isopropoxide in toluene (0.64ml., 3 equivalents). After 1¼ hours, the mixture was partitioned between water (0.5ml.) and ethyl acetate (1.0ml.), and filtered through "Hyflo," washing the filter pad with ethyl acetate (2 × 4ml.). The organic layer was separated, washed with brine (4ml.), dried over magnesium sulphate and filtered, and the solvent was evaporaated to leave a crude oily product, which was chromatographed on "Florisil" (2g.). Elution with 5–10% ethyl acetate in toluene gave the enol, methyl 15-hydroxy-9α,11α-di(4-phenylbenzoyloxy)-5-cis,13-trans-prostadienoate, $R_F = 0.1$ (5% ethyl acetate in toluene), as a viscous oil.

The crude enol (34mg.) was stirred under argon in a mixture of dry methanol (0.5ml.) and acetone (0.2ml.) with anhydrous potassium carbonate (13mg., 2 equivalents) for 18 hours. The mixture was partitioned between ether (10ml.) and saturated sodium bicarbonate (5ml.), the organic layer was separated, extracted with saturated brine (3ml.), dried over magnesium sulphate and filtered. The solvent was evaporated to give a residue from which the two C-15 epimers of racemic prostaglandin $F_2\alpha$ methyl esters were separated by preparative thin layer chromatography using 3% glacial acetic acid in ethyl acetate. Each C-15 epimer was identical by n.m.r. and mass spectrum with authentic material.

EXAMPLE 3

The process described in Example 2 was repeated, using an equivalent quantity of dimethyl 2-oxo-3-(3-trifluoromethylphenoxy)propylphosphonate in place of dimethyl 2-oxoheptylphosphonate to give:

the enone, methyl 15-oxo-9α,11α-di(4-phenylbenzoyloxy)-16-(3-trifluoromethylphenoxy)-17,18,19,20-tetranor-5-cis,13-trans-prostadienoate, $R_F = 0.85$ (ether). Principal peaks in the n.m.r. spectrum in deuteriochloroform solution (δ values) were:

| 3.53, | 3H | singlet, | methyl ester |
| 4.78, | 2H | singlet, | $-CH_2-O-$ |
| 5.2–5.6, | 4H | multiplet, | $>CH-O-$ and cis olefinic protons |
| 6.44–6.70, | 1H | doublet, | $=CH.CO-$ |
| 7.8–7.98, | 2H | doublet | |
| 8.0–8.2, | 2H | doublet | |
| 6.9–7.7, | 19H, | multiplet, | rest of aromatic, and C-13 protons |

and the enol, methyl 15-hydroxy-9α,11α-di-(4-phenylbenzoyloxy)-16-(3-trifluoromethylphenoxy)-17,18,19,20-tetranor-5-cis, 13-trans prostadienoate, $R_F = 0.1$ (5% ethyl acetate in toluene) or 0.8 (ether).

The enol was stirred at room temperature under argon in a mixture of methanol (4.0ml.), water (1.5ml.) and acetone (2.0ml.) with potassium hydroxide (112mg., approximately 10 equivalents) for 16 hours. The solvents were evaporated under reduced pressure and the residue was partitioned between water (12ml.) and ether (3 × 10ml.). The aqueous layer was separated and filtered through "Hyflo," washing the filter pad with water (2ml.). The filtrate was acidified to pH 1 with 2N hydrochloric acid and extracted with ether (3 × 10ml.). The combined ether extracts were washed with brine (5ml.), dried over magnesium sulphate and filtered, and the solvent was evaporated to leave a solid residue consisting of 4-phenylbenzoic acid and a mixture of the C-15 epimers of 9α,11α,15-trihydroxy-16-(3-trifluoromethylphenoxy)-17,18,19,20-tetranor-5-cis,13-trans-prostadienoic acid. The epimers were separated from the 4-phenylbenzoic acid on a Merck silica gel 245 column (50:1) eluting with 5% glacial acetic acid in ethyl acetate. Each epimer was identical by thin layer chromatography with authentic material, $R_F = 0.3$ and 0.4 (3% glacial acetic acid in ethyl acetaate). acetate).

EXAMPLE 4

The dimethyl acetal, methyl 7-[2β-dimethoxymethyl-3α,5α-dihydroxycyclopent-1α-yl]hept-5-cis-enoate (90mg.) was stirred under argon in a mixture of 2% isopropanol in chloroform (4.5ml.) and 1:1 aqueous hydrochloric acid (2.25ml.) for 12 minutes. The organic layer was separated, and the aqueous layer was extracted with chloroform (5ml.). The combined organic extracts were then partitioned with ethyl acetate (5ml.) and saturated sodium carbonate (4ml.). The organic layer was separated, washed with saturated brine (4ml.) and dried and the solvents were evaporated to give the aldehyde, methyl 7-[2β-formyl-3α,5α-dihydroxy-cyclopent-1α-yl]hept-5-cis-enoate, $R_F = 0.2$ (ether). The n.m.r. spectrum in deuteriochloroform showed the following characteristic peaks (δ values):

3.58, 3H, singlet, methyl ester
4.12–4.30, 1H, broad singlet ⎫
4.30–4.55, 1H, broad singlet ⎭ $2 \times >CH-O-$
5.2–5.6, 2H, multiplet, cis olefinic protons
9.78–9.83, 1H, doublet, aldehyde proton The dimethyl acetal used as starting material was prepared as follows:

The acetal, methyl 7-[2β-dimethoxymethyl-3α,5α-di-(4-phenylbenzoyloxy)cyclopent-1α-yl]hept-5-cis-enoate (obtained as described in the last part of Example 1) (500mg.), was stirred at room temperature under argon for 22 hours in a mixture of dry methanol (7.0ml.) and methylene chloride (4ml.) with powdered anhydrous potassium carbonate (205mg. 2 equivalents). The mixture was then acidified to pH 3 with 2N hydrochloric acid (2ml.) and extracted with ethyl acetate (1 × 20ml., 1 × 10ml.). The organic layer was separated and washed successivly with saturated sodium bicarbonate (5ml.) and brine (5ml.). The solution was dried and the solvent was evaporated to yieldd a crude product which after chromatography on "Florisil" (4.5g.), eluting with ether, gave the required starting material.

EXAMPLE 5

A solution of dimethyl 2-oxoheptylphosphonate (134mg.) in dry dimethoxyethane (2.0ml.) was stirred under argon and cooled to −70°C., and a solution of 2.2M butyl-lithium in hexane (234μl.) was added. After a few minutes, the phosphonate anion was treated with a solution of methyl 7-[2β-formyl-3α,5α-dihydroxycyclopent-1α-yl]hept-5-cis-enoate (47mg.) in dimethoxyethane (500μl.) and the cooling bath was removed. After 1½ hours, a few drops of acetic acid were added to adjust the pH to 6, and the solvents were evaporated under reduced pressure. The residue was partitioned with ether (15ml.) and water (10ml.), and the aqueous layer (pH 6) was separated and extracted with ether (10ml.). The combined ether extracts were washed with saturated brine (2 × 5ml.) and dried, and the solvent was evaporated to give an oil which was purified by preparative thin layer chromatography (developed in ethyl acetate) to yield the enone, methyl 9α,11α-dihydroxy-15-oxo-5-cis,13-trans-prostadienoate, $R_F = 0.6$ (3% glacial acetic acid in ethyl acetate).

The n.m.r. spectrum in deuteriochloroform showed the following principal peaks (δ values):
    0.78–1.01, 3H, triplet, C-20 methyl
    3.64, 3H, triplet, methyl ester
    3.85–4.4, 2H, multiplet, >CH—O—
    5.27–5.53, 2H, multiplet, cis olefinic protons
    6.01–6.28, 1H, doublet, C-14 proton
    6.51–6.86, 1H, 2 × doublets, C-13 proton The enone (10mg.) was dissolved in dry toluene (400μl.) by stirring under argon. A 0.323M solution of di-isobornyloxyaluminium isopropoxide (254μl.) was then introduced and stirring was continued for 24 hours. The mixture was then worked up in the manner described for the analogous reaction in Example 2 to give a crude mixture of enol esters which was hydrolysed directly as follows:

The crude enol was stirred in methanol (200μl.) and water (50μl.) containing potassium hydroxide (10mg.). After 1 hour the solvents were evaporated under reduced pressure and the residue was partitioned between water (2ml.) and ethyl acetate (2ml.). The aqueous layer was separated, washed with ether (2ml.), acidified to pH 1 with 2N hydrochloric acid and extracted with ether (2 × 2ml.). The combined ether extracts were dried and the solvent was evaporated to yield a gum comprising the two C-15 epimers of prostaglandin $F_2\alpha$, identical with an authentic sample by thin layer chromatography, n.m.r. and mass spectrometry.

EXAMPLE 6

Methyl 7-[2β-dimethoxymethyl-3α-hydroxy-5α-(4-phenylbenzoyloxy)cyclopent-1α-yl]heptanoate (400mg.) was vigorously stirred under argon for 10 minutes in a two-phase system consisting of 2% isopropanol in chloroform (16ml.) and concentrated hydrochloric acid (8ml.). The total reaction mixture was poured into an excess of saturated bicarbonate and the organic layer was separated. The aqueous solution was extracted with ethyl acetate (3 × 50ml.) and the combined organic extracts were washed with brine (50ml.) and dried, and evaporated to give methyl 7-[2β-formyl-3α-hydroxy-5α-(4-phenylbenzoyloxy)cylopent-1α-yl]heptanoate as a clear oil, $R_F$ 0.2 (ether).

The methyl 7-[2β-dimethoxymethyl-3α-hydroxy-5α-(4-phenylbenzoyloxy)cyclopent-1α-yl]heptanoate, used as starting material in the above process, may be prepared as follows:

To a solution of 7-[2β-dimethoxymethyl-5α-hydroxy-3α-(tetrahydropyran-2-yloxy)cyclopent-1α-yl]hept-5-cisenoic acid (4.9g.) in ether (20ml.) was added an excess of a solution of diazomethane in ether. After 20 minutes at room temperature, the excess of diazomethane was evaporated in a stream of argon, and the ether solution washed with saturated sodium bicarbonate (5ml.). The organic solution was dried and evaporated to dryness to give methyl 7-[2β-dimethoxymethyl-5α-hydroxy-3α-(tetrahydropyran-2-yloxy)cyclopent-1α-yl]hept-5-cis-enoate as a clear oil, $R_F = 0.6$, (5% methanol in methylene dichloride). The n.m.r. spectrum in deuteriochloroform showed the following features (δ values):
    3.4, 6H, singlet, —CH(OCH₃)₂
    3.6, 3H, singlet, —COOCH₃
    4.7, 1H, broad singlet, —CH(OCH₃)₂
    5.45, 2H, multiplet, olefinic protons Methyl 7-[2β-dimethoxymethyl-5α-hydroxy-3α-(tetrahydropyran-2-yloxy)cyclopent-1α-yl]hept-5-cis-enoate (4.3g.) was dissolved in dry pyridine (50ml.) under argon, and treated with p-phenylbenzoyl chloride (4.65g.) and the mixture was stirred for 17 hours. Water (2.5ml.) was then introduced and stirring was continued for 2 hours. The mixture was evaporated under reduced pressure and toluene was added to assist azeotropic removal of the pyridine. The residue was partitioned between toluene (300ml.) and saturated sodium bicarbonate solution (150ml.). The whole mixture was filtered through "Hyflo" and the organic phase was separated. The aqueous layer was extracted with toluene (150ml.), and the organic extracts were combined, washed with brine, (100ml.), dried over sodium sulphate, and filtered and the solvent was evaporated to give methyl 7-[2β-dimethoxymethyl-5α-(4-phenylbenzoyloxy)-3α-(tetrahydropyran-2-yloxy)cyclopent-1α-yl]hept-5-cis-enoate as a clear oil, $R_F = 0.8$ (ether), whose n.m.r. spectrum in deuteriochloroform showed the following features (δ values):
    3.42, 6H, doublet, —CH(OCH₃)₂
    3.6, 3H, singlet, —COOCH₃
    5.4, 2H, multiplet, olefinic protons
    7.2–8.2, 9H, multiplet, aromatic protons A solution of methyl 7-[2β-dimethoxymethyl-5α-(4-phenylbenzoyloxy)-3α-(tetrahydropyran-2-yloxy)cyclopent-1α-yl]hept-5-cis-enoate (6.49g.) in dry methanol (140ml.) was stirred under argon at room temperature with toluene-p-sulphonic acid (9.4ml. of a 1% solution of anhydrous toluene-p-sulfonic acid in dry tetrahydrofuran) for 2.5 hours. Pyridine (5ml.) and toluene (40ml.) were added, and the solvents were evaporated under reduced pressure. The residue was partitioned between ethyl acetate (100ml.) and water (50ml.), and the organic phase was separated, washed successively with saturated sodium bicarbonate (2 × 30ml.) and saturated brine (30ml.) and dried, and the solvents was evaporated to give methyl 7-[2β-dimethoxymethyl-3α-hydroxy-5α-(4-phenylbenzoyloxy)cyclopent-1α-yl]hept-5-cis-enoate as a clear oil, $R_F = 0.4$, (ether), M⁺ (for the trimethylsilyl derivative) = 568.2841 (calculated for $C_{32}H_{44}O_7Si$ = 568.2856).

A solution of methyl 7-[2β-dimethoxymethyl-3α-hydroxy-5α-(4-phenylbenzoyloxy)-cyclopent-1α-yl]hept-5-cis-enoate (1g.) in ethyl acetate (40ml.) was stirred overnight in an atmosphere of hydrogen at room temperature and pressure in the presence of 5% palladium-on-charcoal (500mg.). The catalyst was removed by filtration through "Hyflo" and the solvent was evaporated from the filtrate to give the required methyl 7-[2β-dimethoxymethyl-3α-hydroxy-5α-(4-phenylbenzoyloxy)-cyclopent-1α-yl]heptanoate, $R_F = 0.4$ (ether). The n.m.r. spectrum in deuteriochloroform had the following characteristic signals (δ values):
    3.45, 6H, doublet, —CH(OCH₃)₂
    3.6, 3H, singlet, —COOCH₃
    4.3, 1H, multiplet, >CH.OH
    4.35, 1H, doublet, —CH(OCH₃)₂
    5.42, 1H, multiplet, >CH.OCO—
    7.2–8.2, 9H, multiplet, aromatic protons.

EXAMPLE 7

The process described in the first part of Example 6 was repeated, using methyl 7-[2β-dimethoxymethyl-3α-hydroxy-5α-(4-phenylbenzoyloxy)cyclopent-1α-yl]hept-5-cis-enoate in place of the corresponding heptanoate, to give methyl 7-[2β-formyl-3α-hydroxy-5α-(4-phenylbenzoyloxy)cyclopent-1α-yl]hept-5-cis-enoate as a clear oil, $R_F = 0.2$ (ether). The n.m.r. spectrum in deuteriochloroform showed the following characteristic peaks (δ values):
    3.55, singlet, 3H, methyl ester
    3.5, multiplet, 1H, >CH.OH
    4.5, multiplet, 1H, hydroxy
    5.3, multiplet, 3H, >CH.OCO— and trans-olefinic protons
    7.3–8.2, multiplet, 9H, aromatic protons
    9.9, broad singlet, 1H, aldehyde proton

EXAMPLE 8

7-[2β-Dimethoxymethyl-3α-(3,5-dinitrobenzoyloxy)-5α-hydroxycyclopent-1α-yl]hept-5-cis-enoic acid lactone (322mg.) was vigorously stirred under an argon atmosphere in a mixture of 2% by volume of isopropanol in chloroform (15ml.) and concentrated hydrochloric acid (7.5ml.) for 18 minutes at room temperature. The aqueous layer was separated and extracted with water-washed chloroform (15ml.). The combined chloroform layer and washings were washed successively with aqueous saturated sodium bicarbonate solution (15ml.) and brine (10ml.), and was dried, and the solvent was evaporated under reduced pressure to give 7-[3α-(3,5-dinitrobenzoyloxy)-2β-formyl-5α-hydroxycyclopent-1α-yl]hept-5-cis-enoic acid lactone as an oil which was used without delay in further reaction, $R_F$ = 0.5 (ether). Principal n.m.r. peaks in a spectrum obtained from a deuteriochloroform solution were (δ values):

9.7, double, 1H, aldehyde proton
8.9–9.1, multiplet, 3H, aromatic protons
4.9–5.9, multiplet, 4H, two >CH—O— and two olefinic protons.

The lactone starting material may be obtained as follows:

A solution of 7-[2β-dimethoxymethyl-5α-hydroxy-3α-(tetrahydropyran-2-yloxy)cyclopent-1α-yl]hept-5-cis-enoic acid (1.0g.) in dry pyridine (10ml.) was treated with p-phenylbenzoyl chloride (1.13g.) under an atmosphere of dry argon. Pyridine hydrochloride was precipitated almost immediately, and the mixture was then stirred for 17 hours at room temperature. Water (0.5ml.) was added and stirring was continued for 2 hours. The mixture was evaporated under reduced pressure and the last traces of pyridine were removed by azeotropic distillation with toluene. The residue was partitioned between ether (100ml.) and saturated aqueous sodium bicarbonate solution (50ml.), the mixture was filtered through "Hyflo", the ether layer was separated, and the aqueous layer was re-extracted with ether. The organic layers were combined, washed with saturated brine (50ml.) and dried, and the solvent was evaporated to leave a gum. Chromatography of the gum on "Florisil" (10g.) eluting initially with toluene and finally with 10% v/v ethyl acetate in toluene, afforded 7-[2β-dimethoxymethyl-5α-hydroxy-3α-(tetrahydropyran-2-yloxy)cyclopent-1α-yl]hept-5cis-enoic acid lactone as an oil, $R_F$ = 0.64 and 0.71 (3 runs in chloroform). The n.m.r. spectrum in deuteriochloroform showed the following principal peaks (δ values):

3,35, broad singlet, 7H, methoxy and C-3β protons
3.65–4.7, multiplet, 4H, —CH(OCH₃)₂ and tetrahydropyran C-2 and C-6 protons.
5.0–5.4, multiplet, 3H, >CH.OCO— and olefinic protons.

A solution of the lactone (1.09g.) in dry methanol (17ml.) under argon at room temperature was treated with toluene-p-sulphonic acid monohydrate (60mg.). The mixture was stirred for 30 minutes, treated with pyridine (0.30ml.), and the solvent was evaporated under reduced pressure, last traces of pyridine being removed by azeotropic distillation with toluene. The residue was partitioned between ether (50ml.) and brine (10ml.), the organic layer was separated and dried, and the solvent was evaporated to leave the crude hydroxy-lactone, 7-[2β-dimethoxymethyl-3α,-5α-dihydroxycyclopent-1α-yl]hept-5-cis-enoic acid lactone as an oil, $R_F$ = 0.38 (ether). The n.m.r. spectrum in deuteriochloroform showed the following characteristic peaks (δ values):

3.32, 3H, singlet } methoxy protons.
3.48, 3H, singlet }
3.9–4.2, 1H, multiplet, >CH-OH
4.26, 2H, doublet, —CH(OCH₃)₂
5.0–5.4, 3H, multiplet, C-5β and olefinic protons.

A solution of the hydroxy-lactone (198.4mg.) in dry pyridine (2ml.) was stirred under argon and treated with 3,5-dinitrobenzoyl chloride (250mg.). The mixture was stirred for 30 minutes, and the solvent was evaporated under reduced pressure removing the final traces of pyridine by azeotropic distillation with toluene. The residue was partitioned between toluene (25ml.) and saturated aqueous sodium bicarbonate solution (20ml.), the two-phase mixture was filtered through 'Hyflo', and the toluene layer was separated. The aqueous phase was extracted with more toluene (15ml.) the combined organic layers were extracted with saturated brine (8ml.) and dried, and the solvent was evaporated under reduced pressure to give the required lactone starting material, 7-[2β-dimethoxymethyl-3α-(3,5-dinitrobenzoyloxy)-5α-hydroxycyclopent-1α-yl]hept-5-cis-enoic acid lactone as an oil, $R_F$ = 0.7 (ether). The n.m.r. spectrum in deuteriochloroform showed the following characteristic peaks (δ values):

3.35, 3H, singlet, } methoxy protons
3.39, 3H, singlet, }
4.37, 1H, doublet, —CH(OCH₃)₂
5.0–5.6, 4H, multiplet, >CH—O— and olefinic protons
8.9–9.2, 3H, multiplet, aromatic protons.

EXAMPLE 9

A solution of dimethyl 2-(4-methoxymethylphenyl)-2-oxo-phosphonate (104mg. 1.5 equivalent) in tetrahydrofuran (3.0ml.) was stirred under argon and cooled in a chloroform/'Drikold' bath, and treated with 2.2M butyllithium in hexane (148μl.) followed after a few minutes by a solution of methyl 2β-dimethoxymethyl-3α,5α-di-(4-phenylbenzoyloxy)cyclopent-1α-ylhept-5-cis-enoate (157mg.), also in tetrahydrofuran (2.0ml.). The cooling bath was then removed, and after 2 hours a few drops of acetic acid and then water (200μl.) were added to adjust the pH to about 6. The solvent was evaporated under reduced pressure and the residue was partitioned between water (15ml.) and ethyl acetate (1 × 30ml., 1 × 15ml.). The organic layer was separated, washed with water (10ml.), then dried over magnesium sulphate, and filtered, and the solvent was evaporated to give a viscous oil. This oil was purified by chromatography on "Florisil" (2g.) eluting with 10% ethyl acetate in toluene to afford the enone, methyl 15-(4-methoxymethylphenyl)-15-oxo-9α,11α-di-(4-phenylbenzoyloxy)-16,17,18,19,20-pentanor-5-cis,13-trans-prostadienoate, as an oil, $R_F$ = 0.4 (20% ethyl acetate in methylene dichloride). The n.m.r. spectrum in deuteriochloroform showed the following principal peaks (δ values):

| 3.35, | 3H, | singlet, | methoxy |
|---|---|---|---|
| 3.50, | 3H, | singlet, | —COOCH₃ |
| 4.45, | 2H, | —CH₂OCH₃. | |
| 5.4–5.6, | 4H, | multiplet, | cis olefinic protons and >CH—O— |
| 6.12–7,1 | 1H, | doublet, | =CH.CO— |

| 7.86–8.02, | 2H, | doublet, | |
| 8.02–8.23, | 2H, | doublet | 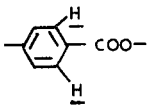 |
| 7.3–7.7, | 15H, | multiplet, | rest of aromatic protons + —C$\underline{H}$=CH.CO— |

Methyl 15-(4-methoxymethylphenyl)-15-oxo-9α,11α-di-(4-phenylbenzoyloxy)-16,17,18,19,20-pentanor-5-cis,13-trans-prostadienoate (110 mg.) was stirred in dry toluene (5.0 ml.) under argon at room temperature, and treated with a 0.323M solution of di-isobornyloxyaluminium isopropoxide in toluene (2.0ml.). After 1¼ hours, the mixture was partitioned between water (0.5ml.) and ethyl acetate (1.0ml.), and filtered through "Hyflo", washing the filter pad with ethyl acetate (2 × 4ml.). The organic layer was separated, washed with brine (4ml.), dried over magnesium sulphate and filtered, and the solvent was evaporated to leave a crude oily product, which was chromatographed on "Florisil" (2g.). Elution with 5–10% ethyl acetate in toluene gave the enol, methyl 15-hydroxy-15-(4-methoxymethylphenyl)-9α,11α-di-(4-phenylbenzoyloxy)-16,17,18,19,20-pentanor-5-cis,13-trans-prostadienoate as a viscous oil, $R_F = 0.4$ (20% ethyl acetate in methylene dichloride).

The crude enol (69mg.) was stirred under argon in a mixture of methanol (4ml.), water (0.7ml.) and N potassium hydroxide (0.9ml.) for 18 hours. The mixture was acidified to pH 5 with oxalic acid, and extracted with ethyl acetate, the extracts were washed with 1:1 saturated brine/water, and dried. Evaporation of the solvents gave a residue, from which the two C-15 epimers of 9α,11α,15-trihydroxy-15-(4-methoxymethylphenyl)-16,17,18,19,20-pentanor-5-cis,13-trans-prostadienoic acid, were separated by thin layer chromatography, using 3% acetic acid in ethyl acetate, $R_F = 0.3$ and 0.4. The n.m.r. spectrum of each epimer in deuterated acetone showed the following characteristic peaks (δ values):

7.2–7.4, 4H, aromatic
5.1–5.6, 4 olefinic protons and —C$\underline{H}$(OH).CH=λCH—
4.4, 2H, —C$\underline{H}_2$.OMe
3.32, 3H, —CH$_2$.O$\underline{Me}$ The mass spectrum showed $(M-CH_3)^+ = 677.3493$, calculated for $C_{35}H_{64}O_6Si_4 = 677.3547$ (for the tetra-trimethylsilyl derivative).

EXAMPLE 10

Dimethyl [2-oxo-3-(indol-5-yloxy)propyl]phosphonate (600mg. 2.5 equivalents) and methyl 7-[2β-formyl-3α-hydroxy-5α-(4-phenylbenzoyloxy)-cyclopent-1α-yl]heptanoate (400mg. 1 equivalent) were suspended under argon in a mixture of toluene (20ml.) and t-butanol (4ml.). Aqueous 1M sodium hydroxide solution (1.84ml., 2.3 equivalents) was added and the two phase mixture was stirred vigorously for 3 hours. The reaction mixture was shaken with ethyl acetate (20ml.) and saturated brine (20ml.), and the organic layer was separated. The aqueous layer was extracted with ethyl acetate (2 × 20ml.), the combined organic extracts were dried, and the solvent was evaporated. Preparative thin layer chromatography gave the enone, methyl 11α-hydroxy-16-(indol-5-yloxy)-15-oxo-9α-(4-phenylbenzoyloxy)-17,18,19,20-tetranor-13-trans-prostenoate as a clear oil, $R_F = 0.3$ (25% ethyl acetate in toluene).

The enone (150mg.) was stirred in dry toluene (5.0ml.) under argon at room temperature, and treated with a 0.323M solution of di-isobornyloxyaluminium isoproxide in toluene (1.16ml., 2 equivalents). After 5 hours, the mixture was partitioned between water and ethyl acetate and filtered through "Hyflo" washing the filter pad with ethyl acetate. The organic layer was separated, washed with brine over magnesium sulphate and filtered, and the solvent was evaporated to leave a crude product, which was purified by thin layer chromatography using 10% ethyl acetate in toluene as the eluant. The enol, methyl 11α,15-dihydroxy-16-(indol-5-yloxy)-9α-(4-phenylbenzoyloxy)-17,18,19,20-tetranor-13-trans-prostenoate, was obtained as a viscous oil, $R_F = 0.1$ (25% ethyl acetate in toluene), whose n.m.r. spectrum in deuteriochloroform showed the following features (δ values):

3.6, 3H, singlet, —COOC$\underline{H}_3$
4.0, 2H, multiplet, —CH(OH).C$\underline{H}_2$O—
4.6, 2H, multiplet, 2 × >C$\underline{H}$.OH
5.4, 1H, multiplet, >C$\underline{H}$.OCO—
5.8, 2H, multiplet, olefinic protons
6.4, 1H, broad singlet, indole C-3 proton
6.8–8.2, 14H, remainder of the aromatic protons plus >N—$\underline{H}$ The enol (128mg.) was stirred at room temperature under argon in a mixture of methanol (15ml.), water (5ml.) and 1,2-dimethoxyethane (15ml.) with potassium hydroxide (400mg.) for 16 hours. Glacial acetic acid was added to adjust the pH of the solution to 6, and the solvents were evaporated under reduced pressure. The residue was partitioned between water and ethyl acetate, and the aqueous layer was acidified to pH 3–4 with 2N oxalic acid. The aqueous layer was separated and washed with ethyl acetate, the combined ethyl acetate solutions were washed with brine and dried, and the solvent was evaporated to leave a solid residue of 4-phenylbenzoic acid and the mixed C-15 epimers of 9α,11α,15-trihydroxy-16-(indol-5-yloxy)-17,18,19,20-tetranor-13-trans-prostenoic acid, $R_F = 0.3$ and 0.45 (3% acetic acid in ethyl acetate).

The n.m.r. spectrum of the more polar C-15 epimer, in deuterated acetone, showed the following characteristic absorptions (δ values):

3.9, 3H, multiplet, C-16 and 1 >C$\underline{H}$.OH protons
4.2, 1H, multiplet,
4.45, 1H, multiplet, } >C$\underline{H}$.OH
5.7, 2H, multiplet, olefinic protons
6.4, 1H, singlet, indole C-3 proton
6.8, 1H, double doublet (J=9 and 3Hz), indole C-6 proton
7.1, 1H, doublet (J= 3Hz), indole C-4 proton
7.3, 2H, multiplet, indole C-2 and C-7 protons,
$M^+ = 719.3924$ (calculated for $C_{36}H_{65}NO_6Si_4 = 719.3890$).

EXAMPLE 11

Dimethyl [3-(3-chlorophenoxy)-2-oxopropyl]phosphonate (140mg. 1.5 equivalents) and methyl 7-[2β-formyl-3α,5α-di-(4-phenylbenzoyloxy)-cyclopent-1α-yl]hept-5-cis-enoate (200mg.) were dissolved in toluene (4ml.). Aqueous 1M sodium hydroxide solution (0.413ml; 1.3 equivalents) was added, and the two phase mixture was stirred vigorously overnight. The organic phase was separated, washed with brine and dried, and the solvent was evaporated. The residue was chromatographed on "Florisil" (15g.) using ether-toluene mixture to elute methyl 16-(3-chlorophenoxy)-

15-oxo-9α,11α-di-(4-phenylbenzoyloxy)-17,18,19,20-tetranor-5-cis,13-trans-prostadienoate, $R_F = 0.8$ (ether).

The latter part of Example 10 was repeated using methyl 16-(3-chlorophenoxy)-15-oxo-9α,11α-di-(4-phenylbenzoyloxy)-17,18,19,20-tetranor-5-cis,13-trans-prostadienoate in place of methyl 11α-hydroxy-16-(indol-5-yloxy)-15-oxo-9α-(4-phenylbenzoyloxy)-17,18,19,20-tetranor-13-trans-prostenoate to give, successively:

the enol, methyl 16-(3-chlorophenoxy)-15-hydroxy-9α,11α-di-(4-phenylbenzoyloxy)-17,18,19,20-tetranor-5-cis,13-trans-prostadienoate, $R_F = 0.4$ (25% petrol ether in ether);

and a mixture of C-15 epimers of 9α,11α,15-trihydroxy-16-(3-chlorophenoxy)-17,18,19,20-tetranor-5-cis,13-trans, prostadienoic acid, $R_F = 0.2$ and 0.3 (3% acetic acid in ethyl acetate) which was purified by thin layer chromatography using 3% acetic acid in ethyl acetate. The n.m.r. spectrum of the mixture of C-15 epimers in deuteriochloroform showed the following characteristic features (δ values):

4.0, multiplet, 4H, —C<u>H</u>₂—O— and >C<u>H</u>(OH)
4.4, multiplet, 1H, >C<u>H</u>(OH)
5.0–5.8, multiplet, 8H, —OH and olefinic protons
6.8–7.3, multiplet, 4H, aromatic protons.

EXAMPLE 12

7-[3α-(3,5-dinitrobenzoyloxy)-2β-formyl-5α-hydroxycyclopent-1α-yl]hept-5-cis-enoic acid lactone (307mg.) was dissolved in toluene (4ml.), the solution was stirred under argon, dimethyl 2-oxo-3-(3-trifluoromethylphenoxy)propylphosphonate (274mg.) was added, then 1M sodium hydroxide (0.72ml.) was added all at once. After 1½ hours more toluene (10ml.) was added, the organic layer was separated, washed with brine (2 × 10ml.) and dried, and the solvent was evaporated to leave an oil which was chromatographed on "Florisil" (6.0g.), eluted with 5% v/v ethyl acetate in toluene, to yield the enone, 11α-(3,5-dinitrobenzoyloxy)-9α-hydroxy-15-oxo-16-(3-trifluoromethylphenoxy)-17,18,19,20-tetranor-5-cis,13-trans-prostadienoic acid 1,9α-lactone as a viscous oil, $R_F = 0.75$ (ether). The n.m.r. spectrum in deuteriochloroform showed the following characteristic peaks (δ values):

8.8–9.1, multiplet, 3H, dinitrobenzoyl protons
6.25, 6.5, doublet, 1H, —CH:C<u>H</u>.CO—
6.6–7.6, multiplet, 5H, —C<u>H</u>:CH.CO— and trifluoromethylphenoxy protons.
4.9–5.6, multiplet, 4H, >C<u>H</u>—O— and cis-olefinic protons
4.6, singlet, 2H, —C<u>H</u>₂—O—

The enone (232.4mg.) was dissolved in dry toluene (6ml.) under argon, treated with 0.27M di-isobornyloxyaluminium isopropoxide (2.44ml., 2 equivalents), and the mixture was stirred for 30 minutes at room temperature. The mixture was partitioned between ethyl acetate (4ml.) and water (2ml.), and filtered through "Hyflo", and the organic layer was separated. The aqueous layer was re-extracted with ethyl acetate (4 × 15ml.) the combined organic layers were washed with brine (10ml.) and dried, and the solvent was evaporated to leave a gum, which was purified by chromatography on "Florisil" (6.0g.) eluting initially with toluene to remove less polar impurities and finally with ether to afford the mixture of epimers of the enol, 11α-(3,5-dinitrobenzoyloxy)-9α,15-dihydroxy-16-(3-trifluoromethylphenoxy)-17,18,19,20-tetranor-5-cis,13-trans-prostadienoic acid 1,9α-lactone, as a yellow foam, $R_F = 0.70$ (ether). The n.m.r. spectrum in deuteriochloroform showed the following characteristic peaks (δ values):

8.9–9.2, multiplet, 3H, dinitrobenzoyl protons
7.4–6.8, multiplet, 4H, trifluoromethylphenoxy protons
5.7–5.9, multiplet, 2H, trans-olefinic protons
5.0–5.6, multiplet, 4H, >C<u>H</u>.O— and cis-olefinic protons
4.3–4.8, multiplet, 1H, >C<u>H</u>(OH)
3.9–3.97, doublet, 2H, —C<u>H</u>₂—O—

The enol (130mg.) was stirred with finely ground anhydrous potassium carbonate (30mg.) in methanol (2.0ml.). After 45 minutes, the dark purplish mixture was adjusted to pH 4 with dilute hydrochloric acid and the solvent was evaporated under reduced pressure. The residue was dissolved in ether (15ml.), and the solution was extracted with sodium bicarbonate solution (5ml.), then with brine (5ml.), and was dried. The solvent was evaporated to leave a residue which was purified by thin layer chromatography to give a mixture of the C-15 epimers ($R_F = 0.55$, 0.65 in ethyl acetate) of the enol lactone 9α,11α,15-trihydroxy-16-(3-trifluoromethylphenoxy)-17,18,19,20-tetranor-5-cis,13-trans-prostadienoic acid 1,9α-lactone as an oil. The n.m.r. spectrum in deuterichloroform showed the following characteristic peaks (δ values):

7.0–7.8, multiplet, 4H, aromatic protons
5.6–5.8, multiplet, 3H, >C<u>H</u>.O— and cis-olefinic protons
4.4–4.6, multiplet, 1H, >C<u>H</u>(OH)
3.8–4.2, multiplet, 3 H, —O—C<u>H</u>₂— and >C<u>H</u>(OH)

The mixture of C-15 epimers of the enol lactone (10mg.) was stirred at room temperature under argon in a mixture of methanol (3ml.), acetone, (3ml.) and water (3ml.). 1M Potassium hydroxide (0.225ml.) was added and the solution was stirred for 16 hours. The mixture was neutralised with glacial acetic acid and the solvents were evaporated under reduced pressure. The residue was dissolved in water (2ml.), adjusted to pH 3 with saturated aqueous oxalic acid and extracted with a mixture of ethyl acetate and ether (1:1) (4 × 5ml.). The combined organic extracts were washed with brine dried over sodium sulphate and filtered, and the solvent was evaporated to give a mixture of C-15 epimers of 9α,11α,15-trihydroxy-16-(3-trifluoromethylphenoxy)-17,18,19,20-tetranor-5-cis,13-trans-prostadienoic acid, $R_F = 0.3$ and 0.4 (3% glacial acetic acid in ethyl acetate). The n.m.r. spectrum in deuterioacetone showed the following characteristic peaks (δ values):

3.8–4.6, multiplet, 5H, —O—C<u>H</u>₂— and >C<u>H</u>(OH)
5.2–5.65, multiplet, 2H, cis-olefinic protons
5.65–5.8, multiplet, 2H, trans-olefinic protons
7.2–7.8, multiplet, 4H, aromatic protons.

EXAMPLE 13

Dimethyl 2-oxoheptylphosphonate (820mg.) and methyl 7-[2β-formyl-3α-hydroxy-5α-(4-phenylbenzoyloxy)-cyclopent-1α-yl]hept-5-cis-enoate (1g.) were suspended under argon in a mixture of toluene (40ml.). Aqueous 1M sodium hydroxide solution (3.9ml.) was added and the two phase mixture was stirred vigorously for 16 hours. The reaction mixture was shaken with ethyl acetate (20 ml.) and saturated brine (20ml.), and the organic layer was separated. The aqueous layer was extracted with ethyl acetate (2 × 40ml.), the combined organic extracts were dried, and the solvent was evaporated. Preparative thin layer chromatography gave the enone, methyl 11α-hydroxy-15-oxo-9α-(4-phenylbenzoyloxy)-5-cis,13-trans-prostadienoate, as a clear oil, $R_F = 0.8$ (ether). M⁺ for the trimethylsilyl derivative = 618.3366, calculated for $C_{37}H_{50}O_6Si = 618.3376$.

The enone (770mg.) was stirred in dry toluene (21ml.) under argon at room temperature, and treated with a 0.323M solution of di-isobornyloxyaluminium isopropoxide in toluene (11ml., 2.5 equivalents). After 16 hours, the mixture was partitioned between water and ethyl acetate and filtered through "Hyflo", washing the filter pad with ethyl acetate. The organic layer was separated, washed with brine, dried over magnesium sulphate and filtered, and the solvent was evaporated to leave a crude product, which was purified by thin layer chromatography using ether as the eluant. The enol, methyl 11α,15-dihydroxy-9α-(4-phenylbenzoyloxy)-5-cis,13-trans-prostadienoate was obtained as an oil $R_F = 0.3$ and 0.2 (ether); M$^+$ for the trimethylsilyl derivative = 692.3949 (calculated for $C_{40}H_{60}O_6Si_2$ = 692.3929), together with a minor amount of the corresponding isopropyl ester.

To a solution of the epimeric diols (605mg.) in methylene dichloride (20ml.) under an atmosphere of nitrogen at 0°C., were added successively redistilled 2,3-dihydropyran (1.2g.) followed by a solution of toluene-p-sulphonic acid (0.3ml. of a 1% solution in tetrahydrofuran). After 10 minutes, a few drops of pyridine were added, and the solution was washed successively with saturated sodium bicarbonate solution and saturated brine, and was dried. Evaporation of the solvents gave a mixture of C-15 epimeric bis(tetrahydropyranyl ethers), methyl 11α,15-bis(tetrahydropyran-2-yloxy)-9α-(4-phenylbenzoyloxy)-5-cis,13-trans-prostadienoate, together with a small amount of the corresponding isopropyl ester, as an oil $R_F = 0.8$ (ether).

The epimeric bis(tetrahydropyran-2-yl ethers) (736mg.) were stirred at room temperature under argon in a mixture of methanol (15ml.), water (15ml.), and 1,2-dimethoxyethane (50ml.) with potassium hydroxide (10.7ml. of a 1M solution in methanol, 10 equivalents) for 16 hours. Glacial acetic acid was added to adjust the pH of the solution to 7 and the solvents were evaporated under reduced pressure. The residue was partitioned between water and ether: pentane (1:1), and extracted with ether:pentane (1:1), (6 × 25 ml.). The combined organic phases were washed with brine and dried, and the solvent was evaporated to give the mixed C-15 epimers of 9α-hydroxy-11α,15-bis(tetrahydropyran-2-yloxy)-5-cis-13-trans-pentadienoic acid together with a small amount of 4-phenylbenzoic acid.

The above mixture (190mg.) was dissolved in pure acetone (2ml.) and cooled to −25°C., Jones' reagent (chromic acid in acetone, 0.118ml.) was added and the solution was stirred for 15 minutes while the temperature reached −10°C. Isopropanol (3 drops) was added, followed by ethyl acetate. The solution was washed with saturated brine and dried, and the solvent was evaporated to give the mixed C-15 epimers of 9-oxo-11α,15-bis(tetrahydropyran-2-yloxy)-5-cis,13-trans-prostadienoic acid as an oil, $R_F = 0.5$ (5% methanol in methylene chloride).

A solution of 9-oxo-11α,15-bis(tetrahydropyran-2-yloxy)-5-cis,13-trans-prostadienoic acid (160mg.) in a mixture of acetic acid (1.3ml.), water (0.6ml.) and tetrahydrofuran (1ml.) was stirred at 40°C. for 2 hours.

The solvents were evaporated to leave a residue consisting of the mixed C-15 epimers of racemic prostaglandin E$_2$ and polymerised dihydropyran. The mixture of C-15 epimers and polymerised material were separated by thin layer chromatography, using 3% glacial acetic acid in ethyl acetate as eluant. The C-15 epimers were identical by n.m.r. spectroscopy with authentic material.

What we claim is:
1. An aldehyde of the formula:

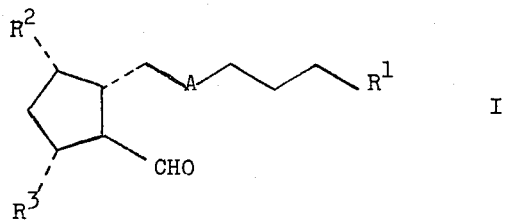

I wherein R$^1$ is carboxy or alkoxycarbonyl of up to 11 carbon atoms, A is cis-vinylene, R$^2$ and R$^3$, which may be the same or different, are hydroxy, 3,5-dinitrobenzoyloxy or hydrocarbon aroyloxy of up to 15 carbon atoms and bearing 0 or 1 alkyl of 1 to 4 carbon atoms on carbon atom 2, 3 or 4.

2. The aldehyde of claim 1 wherein R$^1$ is carboxy, methoxycarbonyl, n-butoxycarbonyl or n-decyloxycarbonyl, A is cis-vinylene, R$^2$ and R$^3$, which may be the same or different, are hydroxy, benzoyloxy, 4-phenylbenzoyloxy or 3,5-dinitrobenzoyloxy and the alkyl substituent which may be present on carbon atom 2, 3 or 4 is methyl.

3. The aldehyde of claim 1 which is selected from methyl 7-[2β-formyl-3α,5α-di(4-phenylbenzoyloxy)-cyclopent-1α-yl]hept-5-cis-enoate, methyl 7-[2β-formyl-3α,5α-dihydroxycyclopent-1α-yl]hept-5-cis-enoate and methyl 7-[2β-formyl-3α-hydroxy-5α-(4-phenylbenzoyloxy)cyclopent-1α-yl]hept-5-cis-enoate.

4. An aldehyde according to claim 1 wherein R$^2$ is hydrocarbon aroyloxy of up to 15 carbon atoms and R$^3$ is hydroxy or hydrocarbon aroyloxy of up to 15 carbon atoms.

5. An aldehyde according to claim 1 wherein R$^2$ is hydrocarbon aroyloxy of up to 15 carbon atoms and R$^3$ is hydroxy.

6. The aldehyde of claim 1 which is methyl 7-[2β-formyl-3α-hydroxy-5α-(4-phenylbenzoyloxy)-cyclopent-1α-yl]hept-5-cis-enoate.

* * * * *